US011992406B2

(12) United States Patent
Gale et al.

(10) Patent No.: US 11,992,406 B2
(45) Date of Patent: May 28, 2024

(54) MULTI-STEP DEPLOYMENT TO IMPROVE TAVR IMPLANT STABILITY

(71) Applicant: St. Jude Medical, Cardiology Division, Inc., St. Paul, MN (US)

(72) Inventors: Caytlin Gale, Minneapolis, MN (US); Gary Erzberger, Plymouth, MN (US); Kristen T. Morin, St. Paul, MN (US); Trevor J. Springer, Stillwater, MN (US); Jaron J. Olsoe, Minneapolis, MN (US); Kristopher Henry Vietmeier, Monticello, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 968 days.

(21) Appl. No.: 16/930,654

(22) Filed: Jul. 16, 2020

(65) Prior Publication Data

US 2021/0068956 A1    Mar. 11, 2021

Related U.S. Application Data

(60) Provisional application No. 62/897,492, filed on Sep. 9, 2019.

(51) Int. Cl.
*A61F 2/24* (2006.01)
*A61F 2/01* (2006.01)
*A61B 17/00* (2006.01)
*A61M 25/02* (2006.01)

(52) U.S. Cl.
CPC ............ *A61F 2/2466* (2013.01); *A61F 2/013* (2013.01); *A61F 2/2418* (2013.01); *A61F 2/2436* (2013.01); *A61B 2017/00243* (2013.01); *A61F 2210/0014* (2013.01); *A61F 2230/0067* (2013.01); *A61F 2250/001* (2013.01);
(Continued)

(58) Field of Classification Search
CPC ...... A61F 2/013; A61F 2/2436; A61F 2/0103; A61F 2/0105; A61F 2/2439
See application file for complete search history.

(56) References Cited

U.S. PATENT DOCUMENTS

| 4,423,730 A | 1/1984 | Gabbay |
|---|---|---|
| 5,078,720 A | 1/1992 | Burton et al. |
| 5,484,444 A | 1/1996 | Braunschweiler et al. |

(Continued)

FOREIGN PATENT DOCUMENTS

| EP | 1129744 A1 | 9/2001 |
|---|---|---|
| EP | 1157673 A2 | 11/2001 |

(Continued)

*Primary Examiner* — Rebecca S Preston
(74) *Attorney, Agent, or Firm* — SLEMAN & LUND LLP

(57) ABSTRACT

A delivery device is configured for aligning and stabilizing a prosthetic heart valve for deployment in a native heart valve annulus. The device includes a catheter assembly having an inner shaft around which a valve compartment is defined, an outer shaft assembled over the inner shaft and adapted to slide relative to the inner shaft, a distal sheath connected to a distal end of the outer shaft and slidable therewith, an outer tube assembled over the outer shaft, and an alignment and stabilization device having a collapsed condition and an expanded condition. The outer tube is adapted to slide relative to the outer shaft to selectively cover and uncover the alignment and stabilization device.

10 Claims, 15 Drawing Sheets

(52) U.S. Cl.
CPC ............... *A61F 2250/0098* (2013.01); *A61M 2025/0293* (2013.01)

(56) References Cited

U.S. PATENT DOCUMENTS

| | | |
|---|---|---|
| 5,702,418 A | 12/1997 | Ravenscroft |
| 5,824,041 A | 10/1998 | Lenker et al. |
| 5,924,424 A | 7/1999 | Stevens et al. |
| 5,968,068 A | 10/1999 | Dehdashtian et al. |
| 5,980,533 A | 11/1999 | Holman |
| 6,269,819 B1 | 8/2001 | Oz et al. |
| 6,306,141 B1 | 10/2001 | Jervis |
| 6,391,050 B1 | 5/2002 | Broome |
| 6,468,299 B2 | 10/2002 | Stack et al. |
| 2006/0106415 A1 | 5/2006 | Gabbay |
| 2006/0142848 A1 | 6/2006 | Gabbay |
| 2006/0167468 A1 | 7/2006 | Gabbay |
| 2007/0073391 A1 | 3/2007 | Bourang et al. |
| 2007/0088431 A1 | 4/2007 | Bourang et al. |
| 2007/0112422 A1 | 5/2007 | Dehdashtian |
| 2007/0162100 A1 | 7/2007 | Gabbay |
| 2007/0168013 A1 | 7/2007 | Douglas |
| 2007/0203575 A1 | 8/2007 | Forster et al. |
| 2007/0239271 A1 | 10/2007 | Nguyen |
| 2008/0147182 A1 | 6/2008 | Righini et al. |
| 2009/0054975 A1 | 2/2009 | del Nido et al. |
| 2011/0224678 A1 | 9/2011 | Gabbay |
| 2011/0282379 A1* | 11/2011 | Lee ................ A61F 2/0105 606/200 |
| 2013/0158654 A1* | 6/2013 | Sutton ................ A61F 2/013 623/2.11 |
| 2014/0249566 A1* | 9/2014 | Quinn ................ A61F 2/01 606/200 |
| 2016/0317276 A1* | 11/2016 | Groh ................ A61F 2/013 |

FOREIGN PATENT DOCUMENTS

| | | |
|---|---|---|
| WO | 10051025 A1 | 5/2010 |
| WO | 10087975 A1 | 8/2010 |

* cited by examiner

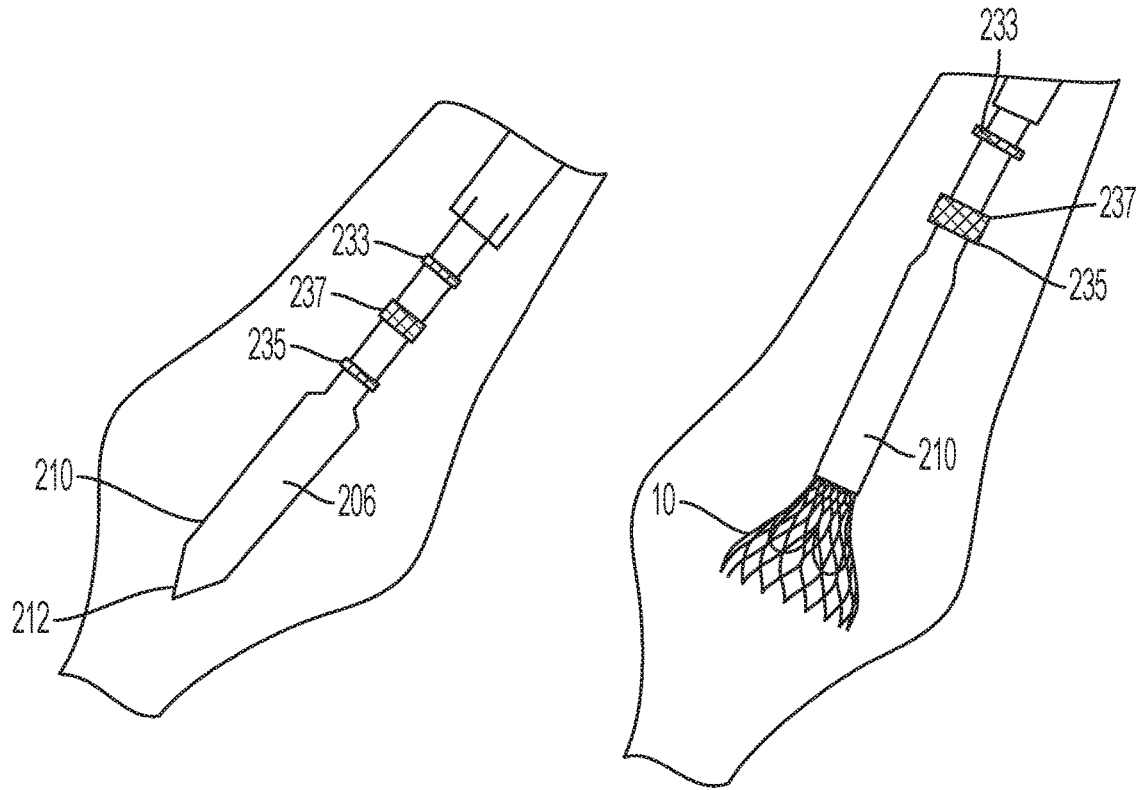
FIG. 5E
FIG. 5F
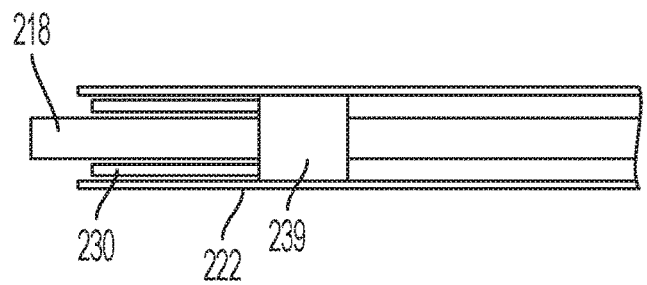
FIG. 5G
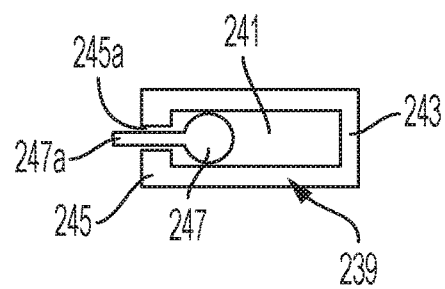
FIG. 5H

MULTI-STEP DEPLOYMENT TO IMPROVE TAVR IMPLANT STABILITY

CROSS-REFERENCE TO RELATED APPLICATIONS

This application claims the benefit of the filing date of U.S. Provisional Patent Application No. 62/897,492 filed Sep. 9, 2019, the disclosure of which is hereby incorporated herein by reference.

BACKGROUND OF THE INVENTION

The present invention relates to collapsible prosthetic heart valve implantation, and more particularly, to apparatus and methods for ensuring proper positioning and stabilization of the prosthetic heart valve during implantation.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed to reduce its circumferential size.

When a collapsed prosthetic valve has reached the desired implant site in the patient (e.g., at or near the annulus of the patient's heart valve that is to be repaired by the prosthetic valve), the prosthetic valve can be deployed or released from the delivery apparatus and expanded to its full operating size. For balloon-expandable valves, this generally involves releasing the entire valve, assuring its proper location, and then expanding a balloon positioned within the valve stent. For self-expanding valves, on the other hand, the stent automatically expands as the stent is withdrawn from the delivery apparatus.

The clinical success of collapsible heart valves is dependent, in part, on the accurate positioning of the valve within the native valve annulus. Inaccurate placement and/or anchoring of the valve may result in the leakage of blood between the prosthetic heart valve and the native valve annulus. This phenomenon is commonly referred to as paravalvular leakage. In aortic valves, paravalvular leakage enables blood to flow from the aorta back into the left ventricle during systole, resulting in reduced cardiac efficiency and strain on the heart muscle.

Despite the various improvements that have been made to transcatheter aortic valve repair devices, conventional delivery devices suffer from various shortcomings. For example, in conventional delivery devices, it may be difficult to correctly position the delivery device at or near the native annulus of the patient and to simultaneously deploy the prosthetic heart valve. Moreover, full deployment of the heart valve sometimes causes the valve to "jump" or reposition when the aortic end of the stent engages with tissue. In these instances, where the valve has been improperly deployed or has moved to an improper position after being fully deployed, the prosthetic heart valve would need to be entirely removed from the patient. Removing a fully deployed prosthetic heart valve requires surgery and greatly increases the risk of damaging the surrounding tissue of an already at risk patient.

Therefore, there is a need for further improvements to the systems and methods for transcatheter delivery of collapsible prosthetic heart valves, and in particular, self-expanding prosthetic heart valves.

BRIEF SUMMARY OF THE INVENTION

In accordance with a first aspect of the present invention, a delivery device is provided for delivering a prosthetic heart valve within a native valve annulus during an implantation procedure. Among other advantages, the device allows the prosthetic heart valve to be properly aligned and stabilized at or near the native valve annulus of the patient before the valve is fully expanded. This ensures that the prosthetic heart valve will be properly positioned prior to deployment and significantly reduces the likelihood that the valve will "jump" or reposition when fully expanded.

One embodiment of the delivery device includes an inner shaft around which a compartment is defined, the compartment being adapted to receive the prosthetic heart valve in an assembled condition; an outer shaft assembled over the inner shaft and adapted to slide relative to the inner shaft along a longitudinal axis thereof; a distal sheath connected to a distal end of the outer shaft and slidable therewith, the distal sheath being adapted to selectively cover and uncover the compartment and the prosthetic heart valve; an alignment and stabilization device having a collapsed condition and an expanded condition, the alignment and stabilization device having one end attached to the outer shaft proximally of the compartment; and an outer tube assembled over the outer shaft and adapted to slide relative to the outer shaft to selectively cover and uncover the alignment and stabilization device.

Another embodiment of the delivery device includes a valve sheath having a lumen configured to receive a collapsible and expandable prosthetic heart valve; an inner member having a length extending along a longitudinal axis, the inner member at least partially disposed within the lumen; and a stabilization device having a collapsed condition and an expanded condition, the stabilization device being attached to the inner member at a predetermined location along the length of the inner member.

A further embodiment of the delivery device includes a delivery tube extending in a longitudinal direction and including a leading portion and a trailing portion, the leading portion and the trailing portion being separable from one another and together defining a lumen configured to receive a heart valve; a deployment device at least partially received within the lumen of the delivery tube, the deployment device including a first member and a second member slidable relative to the first member; a valve including a stent and a valve assembly, the stent including a plurality of struts forming cells and a stabilization device, the stabilization device including a first elongated collapsible and expandable member having an attached end connected to the stent and a free end for engaging tissue.

BRIEF DESCRIPTION OF THE DRAWINGS

Various embodiments of the present invention are described herein with reference to the drawings, wherein:

FIGS. 5C-5L are highly schematic views illustrating variants for coupling the alignment and stabilization device of FIG. 5B to the catheter assembly of FIG. 5A;

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve into a patient, the terms "proximal" and "distal" are to be taken as relative to the user of the delivery devices. "Proximal" is to be understood as relatively close to the operator, and "distal" is to be understood as relatively farther away from the operator.

Figure 1:
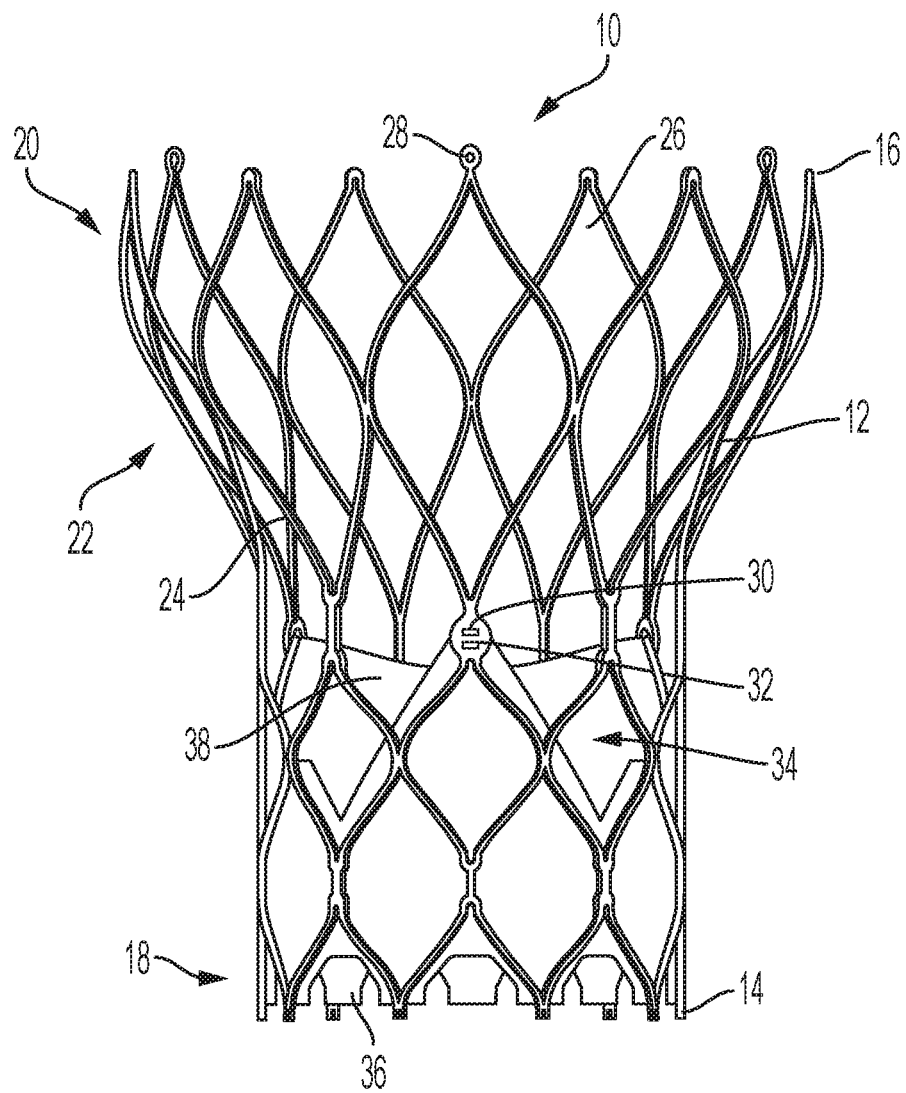
FIG. 1 is a side elevational view of a collapsible prosthetic heart valve in accordance with the prior art.

FIG. 1 illustrates a collapsible prosthetic heart valve 10 that is designed to replace the function of the native aortic valve of a patient. Prosthetic heart valve 10 includes an expandable stent 12 which may be formed from biocompatible materials that are capable of self-expansion, for example, shape memory alloys such as nitinol. Heart valve 10 extends from a proximal or annulus end 14 to a distal or aortic end 16, and includes an annulus section 18 adjacent the proximal end and an aortic section 20 adjacent the distal end. Annulus section 18 has a relatively small cross-section in an expanded condition compared to aortic section 20 in the expanded condition. Annulus section 18 may be in the form of a cylinder having a substantially constant diameter along its length. A transition section 22 tapers outwardly from annulus section 18 to aortic section 20. Stent 12 includes a plurality of struts 24 which form a plurality of cells 26 that are connected to one another in one or more annular rows around the stent. Stent 12 in annulus section 18 may have two annular rows of complete cells and the stent in aortic section 20 and transition section 22 may each have one or more annular rows of partial cells. The cells in aortic section 20 may be larger than the cells in annulus section 18. The larger cells in aortic section 20 facilitate positioning prosthetic valve 10 within the native aortic annulus such that stent 12 does not interfere with blood flow to the coronary arteries.

Stent 12 includes one or more retaining elements 28 at distal end 16. Retaining elements 28 are sized to cooperate with a corresponding retaining structure on a delivery device. This cooperation minimizes axial movement of the prosthetic heart valve relative to the delivery device during unsheathing or resheathing procedures, and prevents rotation of the prosthetic heart valve relative to the delivery device as the delivery device is advanced to the target location and during deployment.

Stent 12 may also include a plurality of commissure attachment features 30 for attaching the commissure between two adjacent leaflets to the stent. As shown in FIG. 1, commissure attachment features 30 may lie at the intersection of four cells 26, two of the cells being adjacent to one another in the same annular row, and the other two cells being in different annular rows and lying in an end-to-end relationship. Commissure attachment features 30 are preferably positioned entirely within annulus section 18, or at the juncture of the annulus section and transition section 22. Commissure attachment features 30 may include one or more eyelets 32 which facilitate the suturing of the leaflet commissure to stent 12.

Prosthetic heart valve 10 also includes a valve assembly 34, which may be positioned entirely within annulus section 18 and secured to stent 12 by suturing the valve assembly to struts 24 and/or to commissure attachment features 30. That is, the entire valve assembly 34 is axially positioned between the proximal end 14 of stent 12 and commissure attachment features 30, such that none of the valve assembly is positioned between the commissure attachment features and the distal end 16 of the stent. Valve assembly 34 includes a cuff 36 and a plurality of leaflets 38 which open and close collectively to function as a one-way valve. Since FIG. 1 illustrates a prosthetic heart valve for replacing a native tricuspid valve, such as the aortic valve, valve 10 is illustrated with three leaflets 38, as well as three commissure attachment features 30. However, it will be appreciated that prosthetic heart valves may have a greater or lesser number of leaflets 38 and/or commissure attachment features 30. Both cuff 36 and leaflets 38 may be wholly or partly formed of any suitable biological material, such as bovine or porcine pericardium, or biocompatible polymers, such as PTFE, urethanes and the like.

Prosthetic heart valve 10 may be delivered to the desired site (e.g., at or near the native aortic annulus) using any one of the delivery devices described in detail below. The delivery device may be introduced into the patient using a transfemoral, transapical or transseptal approach, or another approach. Once prosthetic heart valve 10 is properly positioned inside the native aortic annulus of the patient, it works as a one-way valve, allowing blood to flow into the aorta and preventing blood from returning to the left ventricle.

Figure 2:
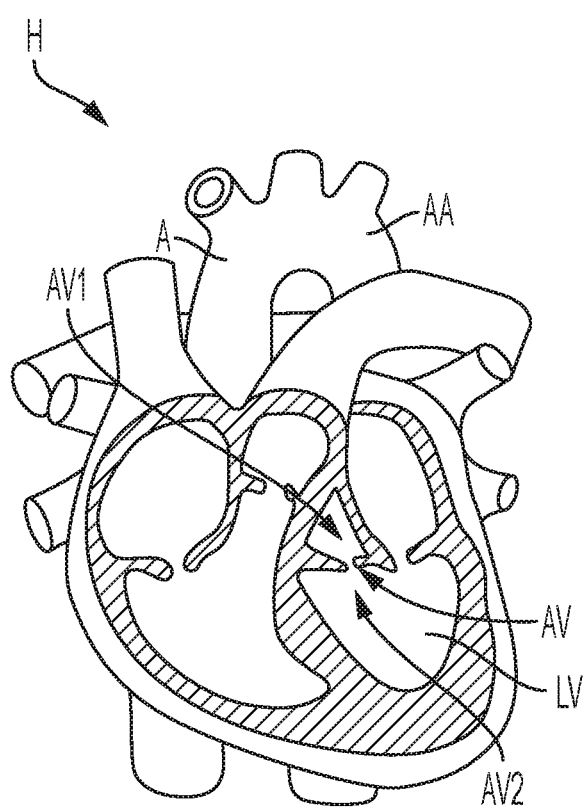
FIG. 2 is a highly schematic cutaway view of the human heart, showing two approaches for delivering a prosthetic aortic heart valve.

FIG. 2 illustrates a human heart H and two different approaches for delivering prosthetic heart valve 10 to its intended target at the aortic valve AV. As illustrated in FIG. 2, heart H includes aorta A, aortic arch AA and left ventricle LV. Two separate paths are shown for introducing prosthetic heart valve 10 to the aortic valve AV. A transfemoral approach for delivering the prosthetic heart valve is indicated by the dashed arrow labeled "AV1". In this method, prosthetic heart valve 10 is inserted into the femoral artery, tracked through the vasculature and then introduced to the target site via aortic arch AA. Echocardiography and other means may be used to help guide the delivery device through this approach. A second dashed arrow, labeled "AV2," indicates a transapical approach for delivering the prosthetic heart valve. In transapical delivery, a small incision is made between the ribs and into the apex of left ventricle LV to deliver the prosthetic heart valve to the target site.

Figure 3:
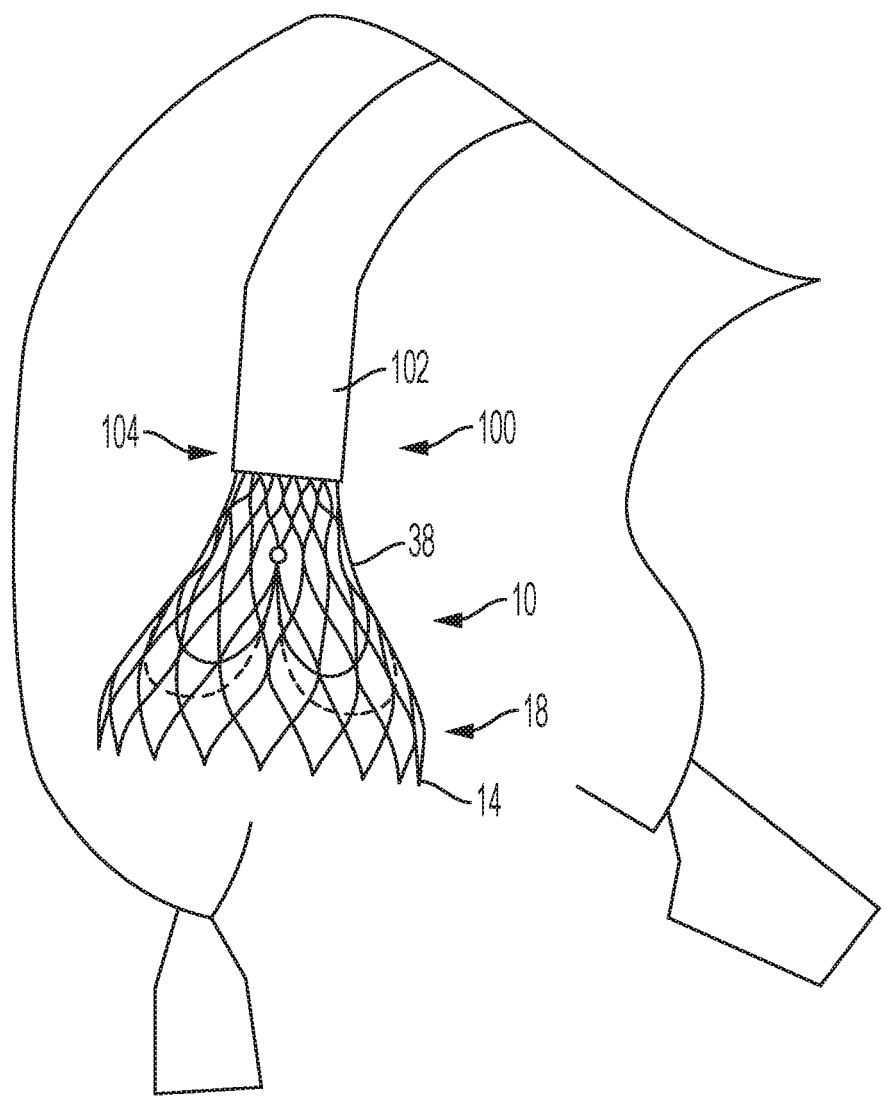
FIG. 3 is a highly schematic fragmentary view showing the partial deployment of a collapsible prosthetic heart valve from a conventional delivery device using a transfemoral approach.

FIG. 3 illustrates prosthetic heart valve 10 being delivered to the aortic valve AV of a patient within a conventional delivery device 100 using a transfemoral approach. During advancement, prosthetic heart valve 10 is disposed in a compartment within delivery device 100 and held in a collapsed configuration by distal sheath 102, with annulus section 18 closest to the distal or leading end 104 of the distal sheath. In the transfemoral approach, the annulus section 18 of heart valve 10 is unsheathed first, thus allowing the annulus section to expand prior to full deployment of the valve. For example, distal sheath 102 may be retracted proximally, toward the user, while internal components (not shown) of delivery device 100 hold prosthetic heart valve 10 stationary. The aortic section 20 of valve 10 remains at least partially covered and constrained by distal sheath 102, while the annulus section 18 of the valve fully expands. In this manner, the function of leaflets 38 may be tested without fully deploying heart valve 10. Unlike the transapical approach, in which prosthetic heart valve 10 is delivered through the apex of left ventricle LV and along a generally linear path to aortic valve AV, the transfemoral approach requires that the delivery device be bent through the aorta. As seen in FIG. 3, due to the anatomical curvature of aortic arch AA, it is more difficult to properly align distal sheath 102, and in turn prosthetic valve 10, within the annulus of the native aortic valve using a transfemoral approach than it is to align the prosthetic valve within the native aortic annulus using a transapical approach.

Even if a surgeon is able to properly navigate aortic arch AA and align prosthetic heart valve 10 within the aortic annulus prior to its deployment, self-expanding prosthetic valves are subject to "jump" when the aortic section 20 of the valve engages tissue. Such repositioning may occur irrespective of whether a transfemoral, transapical or other approach is used.

Figure 4:
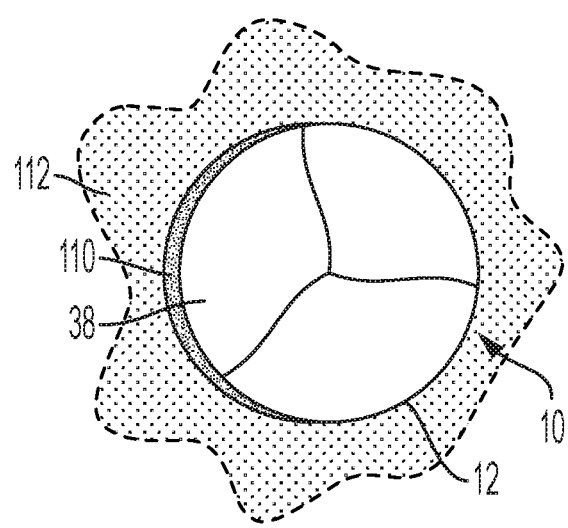
FIG. 4 is a highly schematic cross-section of the collapsible prosthetic heart valve of FIG. 1 mispositioned within the aortic valve annulus of a patient.

FIG. 4 is a highly schematic cross-section of prosthetic heart valve 10 mispositioned within the native aortic annulus of a patient. Mispositioning may occur as a result of delivery device 100 being misaligned with respect to the native aortic annulus when prosthetic valve 10 is deployed, or as a result of the prosthetic heart valve being repositioned as the valve contacts tissue. As seen in FIG. 4, a gap 110 is formed between mispositioned prosthetic valve 10 and native valve annulus 112. Gap 110 may result in paravalvular leakage, enabling blood to flow through the gap from the aorta into the left ventricle during systole. Such leakage may reduce cardiac efficiency and increase strain on the heart muscle.

Figure 5A:
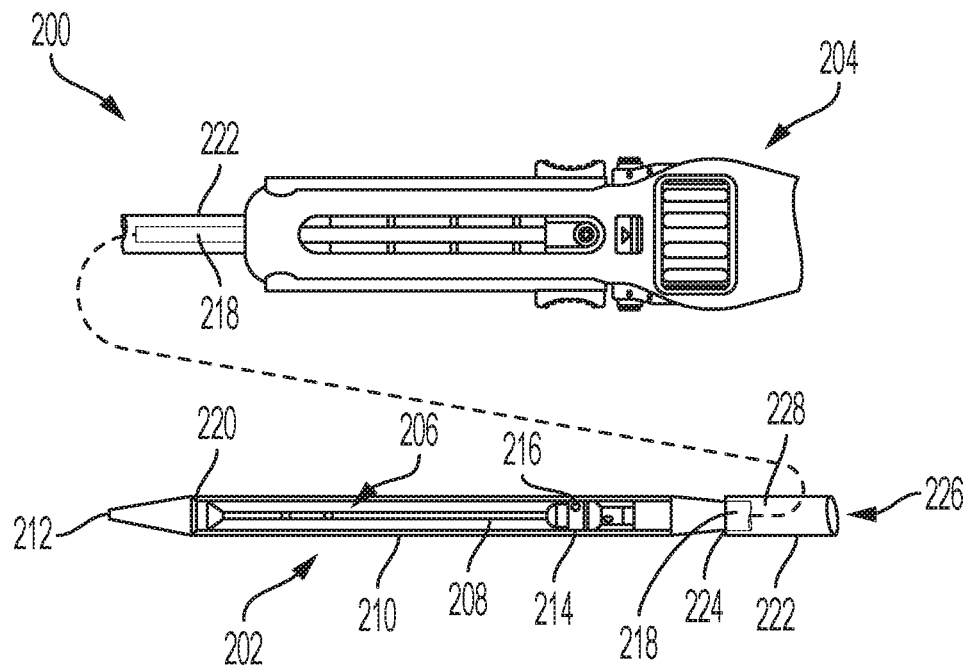
FIG. 5A is a highly schematic view of a portion of a delivery device for a collapsible prosthetic heart valve, shown with a partial longitudinal cross-section of the distal portion of a catheter assembly of the delivery device in accordance with an embodiment of the present invention.
Figure 5B:
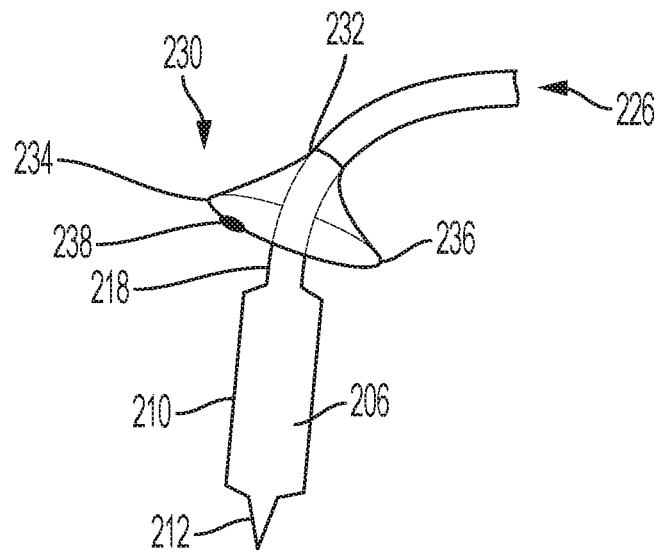
FIG. 5B is a highly schematic side elevational view showing the deployment of an alignment and stabilization device from the delivery device of FIG. 5A.

FIG. 5A illustrates a delivery device 200 according to one embodiment of the invention. Delivery device 200 allows a prosthetic heart valve, such as prosthetic heart valve 10, to be properly positioned and aligned within a native heart valve annulus of the patient before the heart valve is deployed. Delivery device 200 has a catheter assembly 202 for delivering heart valve 10 to and deploying the heart valve at a target location, and an operating handle 204 for controlling deployment of the valve from the catheter assembly. Catheter assembly 202 is adapted to receive prosthetic heart valve 10 in a compartment 206 defined around an inner shaft 208 and covered by a distal sheath 210. An atraumatic tip 212 is provided at the distal end of catheter assembly 202.

Inner shaft 208 may extend from operating handle 204 through catheter assembly 202 to the atraumatic tip 212 of the delivery device, and includes a retainer 214 affixed thereto at a spaced distance from the atraumatic tip. Retainer 214 may have recesses 216 therein that are adapted to receive corresponding retaining elements 28 of prosthetic heart valve 10. The engagement of retaining elements 28 in recesses 216 minimizes longitudinal movement of prosthetic heart valve 10 relative to the inner shaft 208 during unsheathing and prevents rotation of the prosthetic heart valve relative to the inner shaft as delivery device 200 is advanced toward the target location.

Distal sheath 210 surrounds inner shaft 208 and is slidable relative to the inner shaft such that it can selectively cover or uncover compartment 206. Distal sheath 210 is affixed at its proximal end to an outer shaft 218, the proximal end of which is connected to operating handle 204. The distal end 220 of distal sheath 210 abuts atraumatic tip 212 when the distal sheath is fully covering compartment 206, and is spaced apart from the atraumatic tip when the compartment is at least partially uncovered. Handle 204 is adapted to control the deployment of prosthetic heart valve 10 from compartment 206 by permitting the user to selectively slide outer shaft 218 proximally or distally relative to inner shaft 208, thereby respectively uncovering or covering the compartment with distal sheath 210.

An outer tube 222 extends over outer shaft 218 from handle 204 to a distal or leading end 224 that abuts the proximal end of distal sheath 210 in a closed condition. Outer tube 222 has a lumen 226 that is sized to define an annular space 228 between outer shaft 218 and the outer tube. Annular space 228 is sized to house an alignment and stabilization device 230 in a collapsed state between outer shaft 218 and outer tube 222.

Alignment and stabilization device 230 has a first end 232 coupled to catheter assembly 202 and a second end 234. The first end 232 of device 230 may be coupled to outer shaft 218 at a spaced distance proximally of distal sheath 210 and in a manner that allows the alignment and stabilization device to move at least a limited distance in the axial direction with respect to the outer shaft. The second end 234 of device 230 extends distally toward distal sheath 210, and in an expanded state forms an annular ring 236 around outer shaft 218 at or near the junction of the outer shaft and distal sheath 210.

Figure 5C:
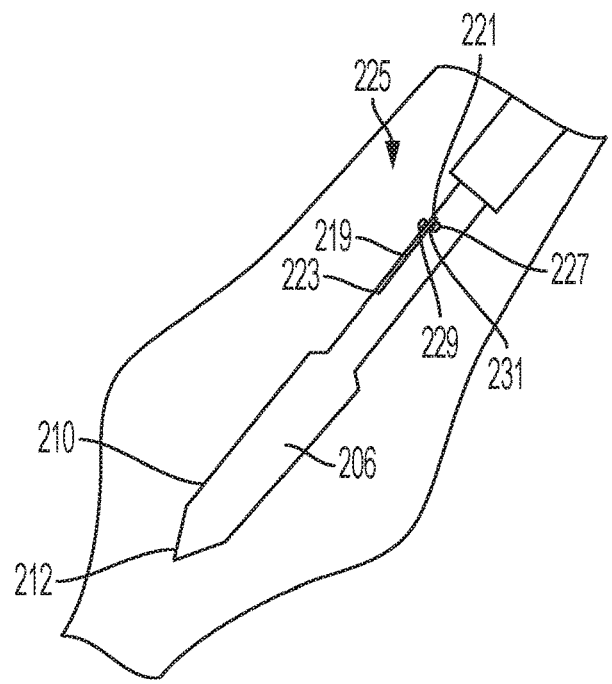
Figure 5D:
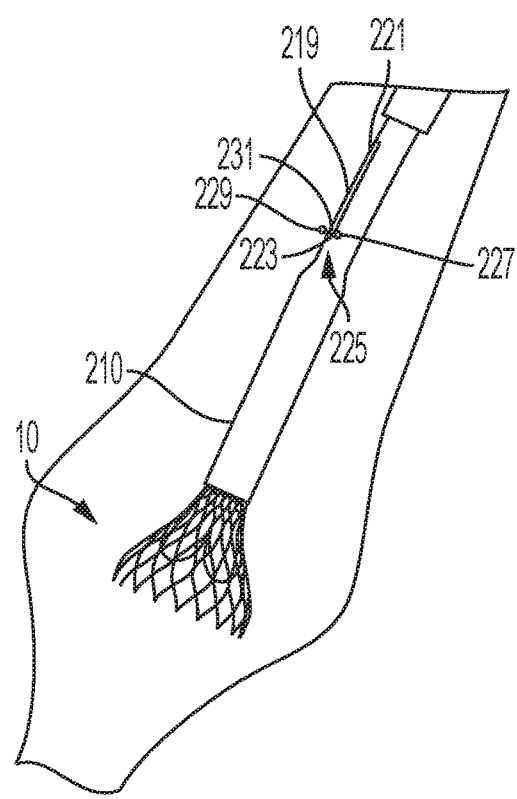

An exemplary mechanism by which the first end 232 of alignment and stabilization device 230 may be coupled to catheter assembly 202 is shown in FIGS. 5C and 5D. It will be understood that alignment and stabilization device 230 is not illustrated in FIGS. 5C and 5D for the purpose of more clearly depicting the features described below.

In this exemplary mechanism, outer shaft 218 has a slot 219 extending through the wall of the outer shaft in an axial direction. The proximal end of slot 219 defines a proximal stop 221, and the distal end of the slot defines a distal stop 223. A retainer 225 is provided within slot 219. Retainer 225 may, for example, include a first ball 227 disposed within the interior of outer shaft 218, a second ball 229 disposed externally of the outer shaft, and a connection member 231 extending through slot 219 and connecting the first and second balls. Retainer 225 is adapted to slide within slot 219 between proximal stop 221 and distal stop 223. Preferably, first ball 227 and second ball 229 co-act with one another to slightly compress the wall of outer shaft 218. In this manner, retainer 225 is able to maintain its position within slot 219 until a force is applied to the retainer that overcomes the compressive force between the first and second balls and causes axial movement of the retainer within the slot. The first end 232 of alignment and stabilization device 230 may be coupled to second ball 229. As a result, movement of retainer 225 within slot 219 will, in turn, result in axial movement of alignment and stabilization device 230 with respect to outer shaft 218. The purpose of enabling the alignment and stabilization device to move axially by some amount relative to outer shaft 218 will become clear from the description of the operation of delivery device 200 below.

Alignment and stabilization device 230 may be formed from a network of braided wires or mesh forming a stent-like device or other structure having cells. Preferably, the braided wires or mesh comprise a biocompatible material that is capable of self-expansion, for example, a shape memory alloy such as nitinol. The nitinol mesh or braid may be configured such that alignment and stabilization device 230 is substantially funnel shaped and coaxially aligned with a longitudinal axis of outer shaft 218 in the expanded condition. Alignment and stabilization device 230 may be radially crimped or collapsed (e.g., toward a longitudinal axis of the stabilization device) to a diameter that allows it to be inserted into the annular space 228 between outer shaft 218 and outer tube 222 for delivery to the deployment site, and then deployed from the lumen 226 of the outer tube and radially expanded to engage tissue.

In some embodiments, alignment and stabilization device 230 may include a plurality of braided layers, each of which may have a funnel shape. For example, an outer braided layer may surround an intermediate braided layer which may surround an innermost braided layer. The innermost braided layer may be formed of a higher density braid than the intermediate braided layer which, in turn, may be formed of a higher density braid than the outer layer. As used herein, braided layers that have a higher density are those that have a greater amount of solid material and a lesser amount of voids per unit of area. As a result of the aforementioned layered structure, alignment and stabilization device 230 may have a relatively dense core that is capable of capturing any emboli in the bloodstream, yet retains sufficient porosity to permit blood flow therethrough. On the other hand, the relatively lower density of the outer layers does not unduly prohibit those layers from crimping to the collapsed configuration.

In order to improve the capturing of emboli and to prevent them from entering the patient's bloodstream, the outermost braided layer of the funnel shaped alignment and stabilization device 230 may be covered with one or more layers of a porous filtering material. Alternatively, the porous filtering material may be placed between any two of the braided layers. Such material may be a porous fabric or a porous polymer film.

A radiopaque marker 238 may be provided on alignment and stabilization device 230, for example on annular ring 236, to allow the alignment and stabilization device to be seen under fluoroscopy and/or echocardiography. Whether located on annular ring 236 or on another portion of delivery device 200, radiopaque marker 238 may be located a predetermined distance from the distal or leading end 220 of distal sheath 210. Radiopaque marker 238 may alternatively be placed, for example, adjacent the leading end of distal sheath 210.

The use of delivery device 200 to align and stabilize a prosthetic heart valve within a native valve annulus of a patient will now be described with reference to FIGS. 6A and 6B. Although delivery device 200 is described as being delivered to the native aortic valve using a transfemoral approach, it will be understood that the delivery device may be used to deliver a prosthetic heart valve to either of the atrioventricular valves using a transfemoral, transapical, or transseptal approach, or another approach.

To load delivery device 200, a physician first collapses and inserts prosthetic heart valve 10 into compartment 206 and moves distal sheath 210 distally to cover the valve. With distal sheath 210 in the closed position, alignment and stabilization device 230 may be coupled to retainer 225. Outer tube 222 may then be slid distally over outer shaft 218 until its leading end 224 abuts or is near to the proximal end of distal sheath 210, collapsing alignment and stabilization device 230 within the lumen 226 of the outer tube. Delivery device 200 may then be percutaneously inserted into the patient and advanced toward the native aortic valve using a conventional transfemoral approach, all while being observed under fluoroscopy. By knowing the predetermined distance between radiopaque marker 238 and the leading end 220 of distal sheath 210, the physician will be able to determine the position (e.g., depth) of the leading end of the distal sheath relative to the native valve annulus and, in turn, when prosthetic heart valve 10 is positioned at the proper depth within that annulus.

Figures 6A, 6B:
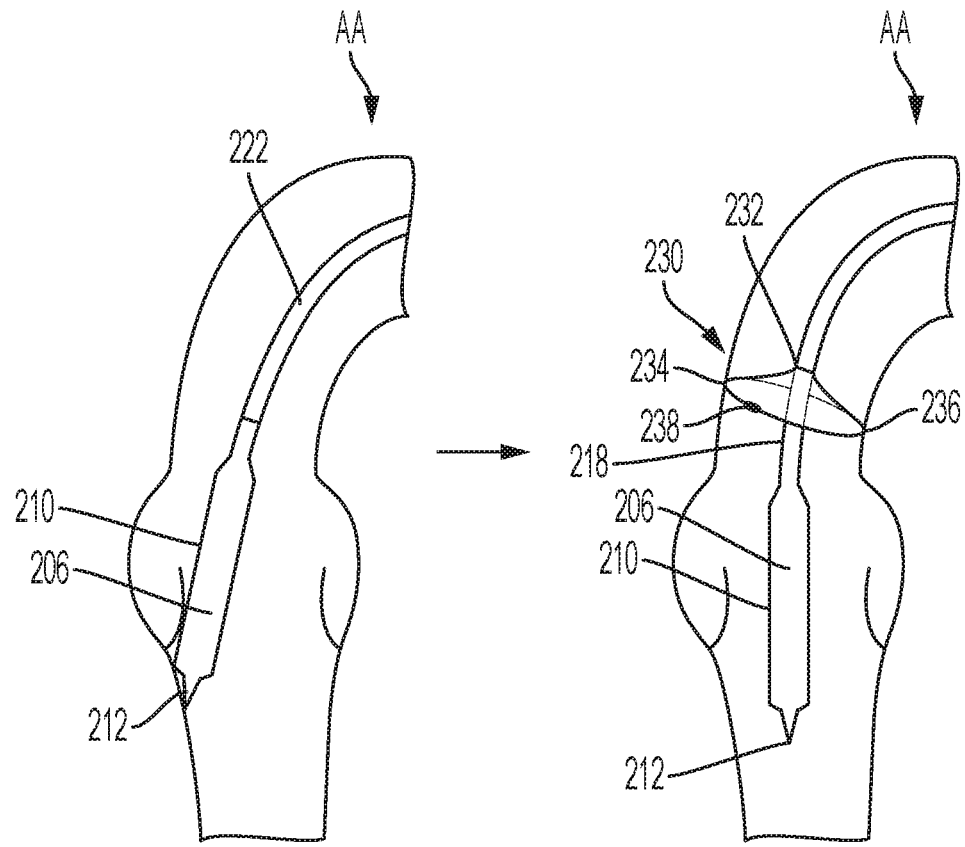
FIGS. 6A and 6B are highly schematic fragmentary views showing the deployment of an alignment and stabilization device in the aorta using the delivery device of FIGS. 5A and 5B and a transfemoral approach.

Referring to FIG. 6A, distal sheath 210 may approach the native aortic valve AV at an angle relative to the native valve annulus due to the anatomical curvature of aortic arch A. To ensure proper alignment of distal sheath 210 with the native aortic valve annulus before the deployment of prosthetic heart valve 10, alignment and stabilization device 230 may first be deployed within the ascending aorta of the patient. Alignment and stabilization device 230 may be deployed by retracting outer tube 222 proximally, exposing the alignment and stabilization device and enabling it to radially expand such that annular ring 236 engages the surrounding aortic tissue. As ring 236 engages the aortic tissue, it will push outer tube 222 and distal sheath 210 away from the tissue until the expansion of the ring is complete and the ring is engaged with aortic tissue all the way around outer shaft 218.

If prosthetic heart valve 10 is not properly positioned within the native valve annulus, the physician may partially advance outer tube 222 over stabilization device 230, which in turn will partially collapse the stabilization device and disengage ring 236 from the surrounding tissue. The physician may then advance or retract delivery device 200 to the proper depth. After the physician has determined that prosthetic heart valve 10 is positioned at the correct depth within the native valve annulus, the physician may again fully deploy stabilization device 230, enabling ring 236 to engage the surrounding tissue and, in turn, center the prosthetic heart valve within the native valve annulus. With ring 236 engaged with cardiac tissue, distal sheath 210, and in turn prosthetic heart valve 10, will be centered relative to the native valve annulus, as seen in FIG. 6B. Ring 236 engages the tissue of the left ventricular outflow tract with a friction force that exceeds the relatively minor friction forces between retainer 225 and slot 219. Distal sheath 210 may then be proximally retracted, exposing the heart valve and enabling it to radially expand into engagement with the native valve annulus.

During the proximal retraction of distal sheath 210, alignment and stabilization device 230 is able to remain stably engaged with the native tissue due to the manner in which the alignment and stabilization device is coupled to outer shaft 218 and due to the fact that the friction between ring 236 and the left ventricular outflow tract exceeds the friction force between retainer 225 and slot 219. Thus, as outer shaft 218 and distal sheath 210 are proximally retracted to deploy prosthetic valve 10, device 230 maintains its position within the left ventricular outflow tract as retainer 225 slides from proximal stop 221 (FIG. 5C) to distal stop 223 (FIG. 5D). As a result, the ring 236 of device 230 will maintain contact with the surrounding tissue and will keep prosthetic heart valve 10 centered in the native valve annulus as it is deployed. Alignment and stabilization device 230 may also absorb a portion of the force that results as the annulus section 18 of prosthetic heart valve 10 contacts the native valve annulus, reducing the likelihood that the prosthetic valve will "jump" during its deployment. After prosthetic heart valve 10 has been implanted, outer tube 222 may be advanced distally over alignment and stabilization device 230 to collapse the alignment and stabilization device within the lumen 226 of outer tube 222, and distal sheath 210 may be advanced distally to close compartment 206. Delivery device 200 may then be removed from the patient.

Variants of the foregoing mechanism are available for coupling alignment and stabilization device 230 to catheter assembly 202 in a manner that allows the alignment and stabilization device to slide in the axial direction with respect to outer shaft 218. Exemplary variants of this coupling are shown in FIGS. 5E-5L.

Referring to FIGS. 5E and 5F, slot 219 in outer shaft 218 may be replaced with a proximal ring 233 that acts as the proximal stop and a distal ring 235 that acts as the distal stop. Proximal ring 233 and distal ring 235 are each fixed to the exterior surface of outer shaft 218 at a location proximal to distal sheath 210. A coupling ring 237 is disposed around the exterior surface of outer shaft 218 between proximal ring 233 and distal ring 235 so as to be slidable between the proximal and distal rings. Preferably, coupling ring 237 is sized so that it exerts a relatively small amount of friction on outer shaft 218. This friction enables coupling ring 237 to maintain its position between proximal ring 233 and distal ring 235 until a force is applied to the coupling ring that overcomes the friction and causes axial movement of the coupling ring relative to outer shaft 218. The first end 232 of alignment and stabilization device 230 may be coupled to coupling ring 237 such that movement of the coupling ring will, in turn, result in axial movement of the alignment and stabilization device between proximal ring 233 and distal ring 235. During deployment of a prosthetic heart valve 10, as outer shaft 218 and distal sheath 210 are proximally retracted, the friction force exerted by coupling ring 237 on outer shaft 218 is exceeded by the friction force between ring 236 and the tissue of the left ventricular outflow tract, enabling the coupling ring to slide from proximal ring 233 toward distal ring 235 as the proximal retraction of the outer shaft and distal sheath continues. As a result, the ring 236 of device 230 will maintain contact with the surrounding tissue and will keep prosthetic heart valve 10 centered in the native valve annulus as it is deployed.

In another variant, shown in FIGS. 5G and 5H, slot 219 in outer shaft 218 may be replaced by a retainer 239 that is fixedly mounted around the exterior surface of the outer shaft. Retainer 239 may have an axial bore therethrough (not shown) for receiving outer shaft 218, and is movable with the outer shaft in an axial direction. Retainer 239 has a slot 241 extending between a proximal wall 243 of the retainer and a distal wall 245 of the retainer. The distal wall 245 of retainer 239 has an opening 245a from slot 241 to an exterior of the retainer. Alignment and stabilization device 230 includes one or more retainer features 247, for example, one or more enlarged balls or disk-shaped structures that each may be mounted to an arm or other structure 247a that extends away from the first end 232 of the device. Arm 247a extends through opening 245a of retainer 239, while retainer feature 247 is sized to be positioned within slot 241 and to slide therein, but is too large to fit through opening 245a. The sliding of retaining feature 247 between the proximal wall 243 of retainer 239 and the distal wall 245 of the retainer will result in axial movement of device 230 with respect to outer shaft 218. During deployment of prosthetic heart valve 10, as outer shaft 218 and distal sheath 210 are proximally retracted to deploy the prosthetic heart valve, the frictional force between ring 236 and the tissue of the left ventricular outflow tract will hold ring 236 in place relative to the tissue as retaining feature 247 slides from proximal wall 243 to distal wall 245 during the proximal retraction of outer shaft 218 and distal sheath 210. As a result, the ring 236 of device 230 will keep prosthetic heart valve 10 centered in the native valve annulus as it is deployed.

Figure 5I:
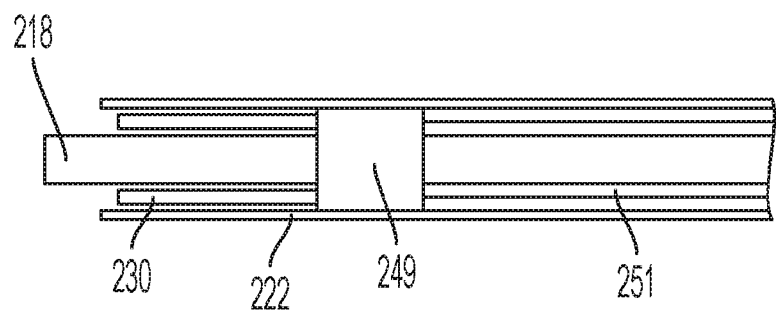
Figure 5J:
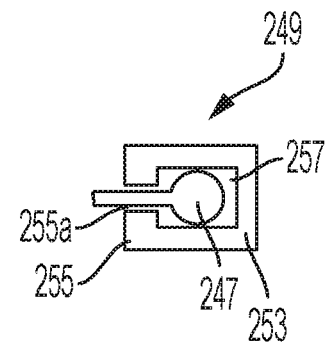

FIGS. 5I and 5J illustrate yet another variant that permits alignment and stabilization device 230 to move axially with respect to outer shaft 218. In this variant, device 230 is not coupled to outer shaft 218. Instead, device 230 is coupled to operating handle 204 via a shortened retainer 249 and one or more rigid wires 251. Shortened retainer 249 may have an axial bore for receiving outer shaft 218, and may be positioned between the outer shaft and outer tube 222, as shown in FIG. 5I. Shortened retainer 249 is similar to retainer 239 described above except that it has a relatively smaller length in the axial direction, and that the axial bore through shortened retainer 249 may have a diameter larger than the outer diameter of outer shaft 218 so that the outer shaft is freely moveable through the retainer. Shortened retainer 249 includes a proximal wall 253, a distal wall 255 having an opening 255a therein, and a receiving space 257 provided between the proximal and distal walls for receiving an enlarged retainer feature 247. However, unlike slot 241 in retainer 239, receiving space 257 is sized to receive retainer feature 247 and secure the retainer feature between the proximal wall 253 and the distal wall 255 such that the retainer feature is not slidable in the receiving space. The one or more rigid wires 251 may axially extend from operating handle 204 and along the outside of outer shaft 218 until reaching shortened retainer 249 to which the wires are attached. Wires 251 support shortened retainer 249 at a fixed position. The first end 232 of alignment and stabilization device 230 is coupled to shortened retainer 249 in a manner that permits outer shaft 218 to be proximally retracted while the shortened retainer and device 230 are held in an axially fixed position. During deployment of prosthetic heart valve 10, as outer shaft 218 and distal sheath 210 are proximally retracted, the outer shaft may slide through the axial bore of shortened retainer 249, which is held stationary relative to the operating handle 204 by rigid wires 251. As a result, the ring 236 of device 230 will maintain contact with the surrounding tissue and will keep prosthetic heart valve 10 centered in the native valve annulus as it is deployed.

Figure 5K:
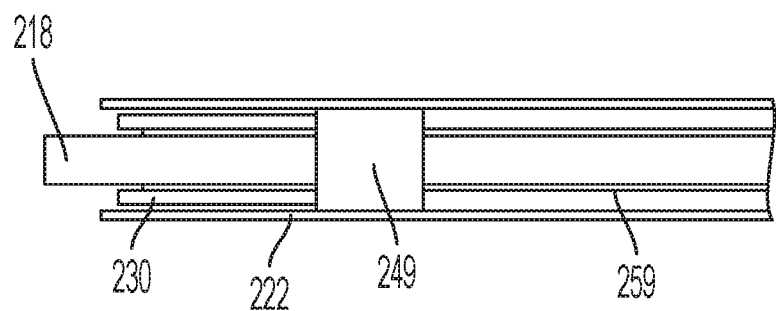

FIG. 5K illustrates a further variant allowing alignment and stabilization device 230 to move axially with respect to outer shaft 218. This variant is similar to the variant described in connection with FIGS. 5I and 5J in that device 230 is again mounted around outer shaft 218 and coupled to operating handle 204 via shortened retainer 249. However, unlike that previously described variant, shortened retainer 249 is coupled to a sleeve 259 that axially extends from operating handle 204 to the shortened retainer. Sleeve 259 supports shortened retainer 249 at a fixed position, and may be disposed between outer shaft 218 and outer tube 222. The first end 232 of alignment and stabilization device 230 is coupled to shortened retainer 249 in a manner that permits outer shaft 218 to be proximally retracted while shortened retainer 249 and device 230 are held in an axially fixed position. During deployment of prosthetic heart valve 10, as outer shaft 218 and distal sheath 210 are proximally retracted, the outer shaft may slide through the axial bore of shortened retainer 249, which is held stationary relative to the operating handle 204 by sleeve 259. Consequently, the ring 236 of device 230 will maintain contact with the surrounding tissue and will keep prosthetic heart valve 10 centered in the native valve annulus as it is deployed.

Figure 5L:
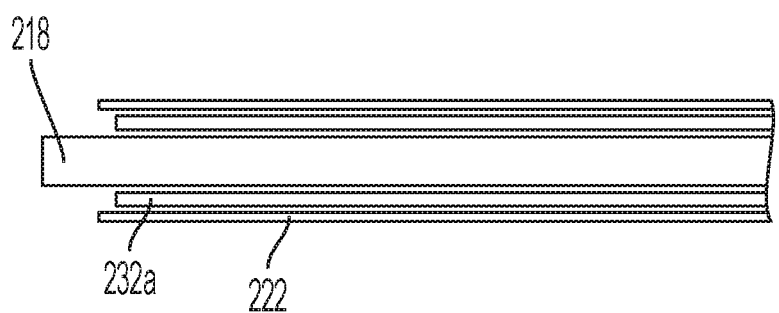

FIG. 5L illustrates yet another variant allowing alignment and stabilization device 230 to move axially with respect to outer shaft 218. This variant is similar to the variant described in connection with FIGS. 5I and 5J in that device 230 is coupled to operating handle 204. However, unlike that previously described variant, device 230 is not indirectly coupled to operating handle 204 by shortened retainer 249. Instead, in this variant, device 230 includes an elongated first end 232a that extends between outer shaft 218 and outer tube 222 and is directly attached to operating handle 204. In this respect, device 230 is fixed relative to operating handle 204. During deployment of prosthetic heart valve 10, as outer shaft 218 and distal sheath 210 are proximally retracted, the outer shaft may slide through the elongated first end 232a of device 230 as the device is held stationary. As a result, ring 236 of device 230 will maintain contact with the surrounding tissue and will keep prosthetic heart valve 10 centered in the native valve annulus as it is deployed.

Figure 7A:
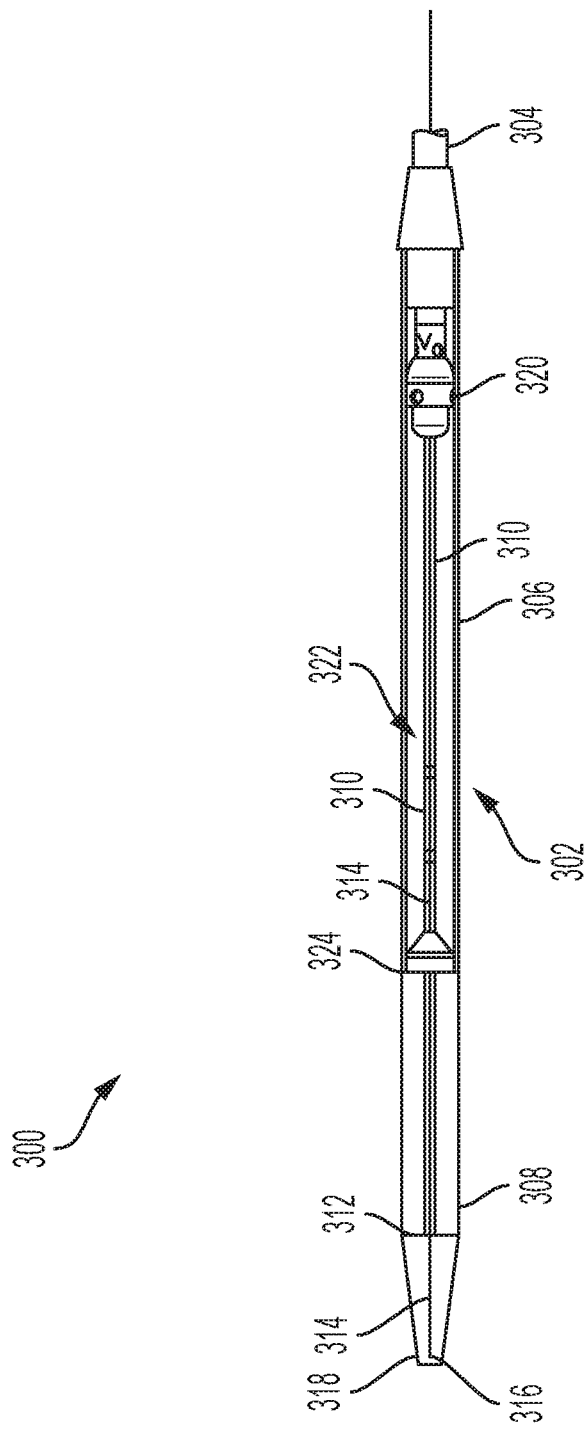
FIG. 7A is a highly schematic view showing a partial longitudinal cross-section of the distal portion of a catheter assembly of a delivery device according to another embodiment of the present invention.
Figure 7B:
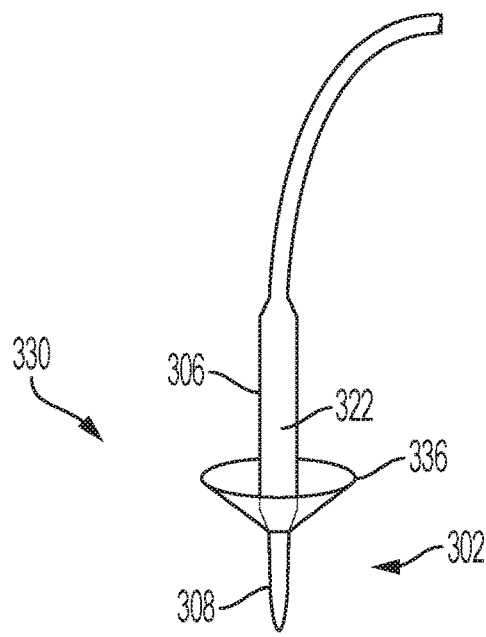
FIG. 7B is a highly schematic side elevational view showing the deployment of an alignment and stabilization device from a delivery device in accordance with another embodiment of the present invention.

FIGS. 7A and 7B illustrate a portion of a catheter assembly 302 of a delivery device 300 according to another embodiment of the invention. Delivery device 300 includes an outer shaft 304 connected at a proximal end to an operating handle (not shown) and at a distal end to a distal sheath 306. An additional sheath section 308, separate from distal sheath 306, may be arranged distally of the distal sheath. A first inner shaft 310 may be connected at its proximal end to the operating handle, and may extend through a lumen in outer shaft 304, and through distal sheath 306 and sheath section 308, to a distal or leading end 312.

A second inner shaft 314 may also be connected at its proximal end to the operating handle, and may extend through a lumen in first inner shaft 310 and out from the distal end 312 thereof. At its distal or leading end 316, second inner shaft 314 may be connected to an atraumatic tip 318. Atraumatic tip 318 is fixedly connected to the distal end of sheath section 308 so that movement of the atraumatic tip in either a proximal or distal direction results in a corresponding movement of the sheath section. A retainer 320 affixed to first inner shaft 310 at a spaced distance from atraumatic tip 318 may include recesses that are adapted to receive corresponding retaining elements 28 of prosthetic heart valve 10. The engagement of retaining elements 28 in the retainer recesses minimizes longitudinal movement of prosthetic heart valve 10 relative to first inner shaft 310 during unsheathing and resheathing operations and prevents rotation of the prosthetic heart valve relative to the first inner shaft as delivery device 300 is advanced toward the target location.

Distal sheath 306 is slidable relative to first inner shaft 310 such that it can selectively cover or uncover a compartment 322 holding prosthetic heart valve 10 in a collapsed condition. Distal sheath 306 fully covers compartment 322 and prosthetic heart valve 10 held therein when the distal end 324 of the distal sheath is in its distalmost position, abutting sheath section 308 when the sheath section is in its proximalmost (closed) position. When sheath section 308 is in its proximalmost (closed) position, compartment 322 is at least partially uncovered when the distal end 324 of distal sheath 306 is spaced apart from the sheath section.

An alignment and stabilization device 330 is positioned in delivery device 300 distally of compartment 322 holding prosthetic heart valve 10, i.e., between the prosthetic heart valve and atraumatic tip 318. Alignment and stabilization device 330 is substantially similar to alignment and stabilization device 230, being different therefrom in the following respects. First, rather than being covered by outer tube 222, the alignment and stabilization device 330 is connected to first inner shaft 310 and held in a collapsed condition by sheath section 308. As a result, delivery device 300 is able to eliminate the outer tube 222 that is present in delivery device 200. In addition, alignment and stabilization device 330 is oriented in the direction opposite device 230. That is, device 330 extends proximally from its connection to first inner shaft 310 to annular ring 336. Sheath section 308 is slidable relative to first inner shaft 310 between a proximalmost position in which the sheath section covers alignment and stabilization device 330 and holds it in a collapsed condition, and a more distal position in which the alignment and stabilization device is at least partially uncovered. Sheath section 308 is moved in a proximal or distal direction through sliding movement of second inner shaft 314 relative to first inner shaft 310.

The use of delivery device 300 to align and stabilize prosthetic heart valve 10 within a native valve annulus of a patient will now be described with reference to FIGS. 8A and 8B. A physician first collapses and assembles prosthetic heart valve 10 around the first inner shaft 310 of catheter assembly 302 and moves distal sheath 306 distally to cover the valve. The physician may then radially crimp or collapse alignment and stabilization device 330, for example using his or her hand, and retracts sheath section 308 proximally to cover the alignment and stabilization device and hold it in the collapsed condition between prosthetic heart valve 10 and atraumatic tip 318. Delivery device 300 may then be percutaneously inserted into the patient and advanced beyond the native valve to be replaced. In replacing the native aortic valve using a transfemoral approach, for example, the capsule may be guided into the left ventricular outflow tract.

Figures 8A, 8B:
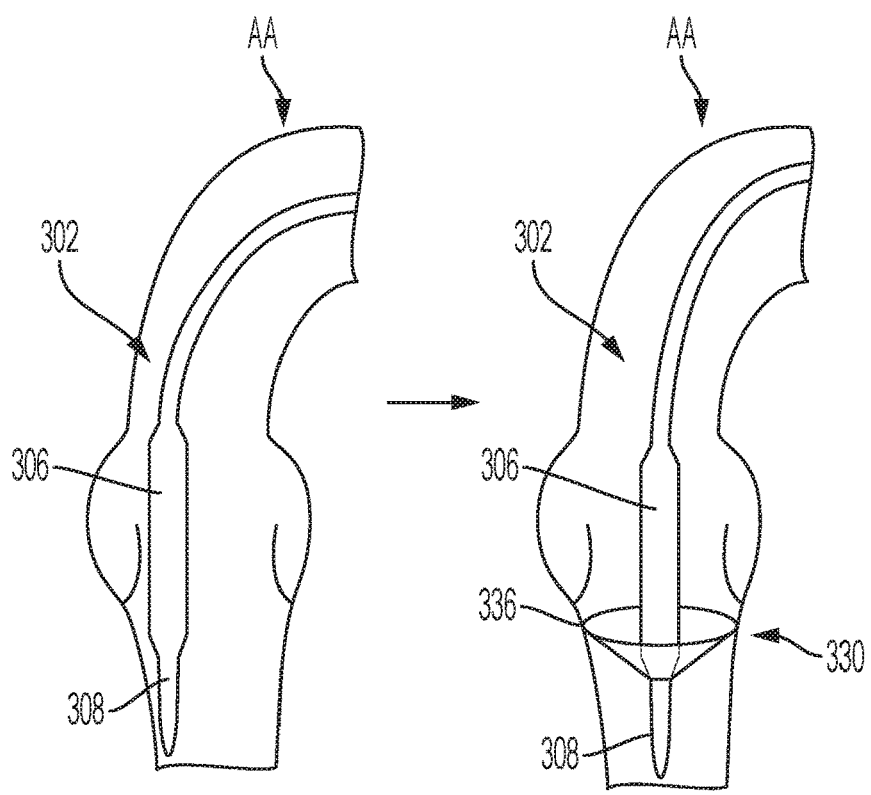
FIGS. 8A and 8B are highly schematic fragmentary views showing the deployment of an alignment and stabilization device in the left ventricular outflow tract using the delivery device of FIG. 7B and a transfemoral approach.

As shown in FIG. 8A, it may be difficult to properly align distal sheath 306 relative to the native aortic annulus because of the natural curvature of aortic arch AA. Once delivery device 300 has been positioned within the left ventricular outflow tract, the device may be retracted to position distal sheath section 308 within the native valve annulus. By knowing the predetermined distance between the radiopaque marker and the leading end 324 of distal sheath 306, the physician will be able to determine the position (e.g., depth) of the leading end of the distal sheath relative to the native valve annulus and, in turn, when prosthetic heart valve 10 is positioned at the proper depth within that annulus. After the physician has determined that prosthetic heart valve 10 is located at the proper depth within the annulus, the physician may use alignment and stabilization device 330 to align distal sheath 306 and the prosthetic heart valve within the annulus.

To correctly align distal sheath 306 with the native aortic annulus before the deployment of prosthetic heart valve 10, alignment and stabilization device 330 may be deployed from sheath section 308 into the left ventricular outflow tract of the patient by distally advancing second inner shaft 314, and with it sheath section 308, to uncover the alignment and stabilization device. When alignment and stabilization device 330 has been fully exposed it will expand until annular ring 336 engages the surrounding tissue of the left ventricular outflow tract, while prosthetic heart valve 10 will still be covered and held in a collapsed condition by distal sheath 306. As ring 336 engages the tissue of the left ventricular outflow tract, it will push first inner shaft 310 and distal sheath 306 away from the tissue until the expansion of the ring is complete and the ring is engaged with tissue of the left ventricular outflow tract all the way around the first inner shaft. With ring 336 engaged with tissue covering the full circumference of the left ventricular outflow tract, distal sheath 306, and in turn prosthetic heart valve 10, will be centered relative to the native valve annulus as seen in FIG. 8B.

After it has been determined that prosthetic heart valve 10 is correctly positioned within the native valve annulus, the physician may proximally retract distal sheath 306 to deploy the prosthetic heart valve. Full deployment of prosthetic heart valve 10 will cause the annulus section 18 of the valve to radially expand and engage the native valve annulus with a force. Engagement of the alignment and stabilization device 330 against the left ventricular outflow tract during deployment of prosthetic heart valve 10 will also help absorb the force resulting from the deployment of the prosthetic heart valve, and reduce the likelihood that the force will reposition prosthetic heart valve 10 within the native valve annulus. After prosthetic heart valve 10 has been implanted, distal sheath 306 may be slid distally to a closed position, and sheath section 308 may be retracted proximally to a closed position, collapsing alignment and stabilization device 330 against first inner shaft 310. Delivery device 300 may then be removed from the patient.

Figure 9:
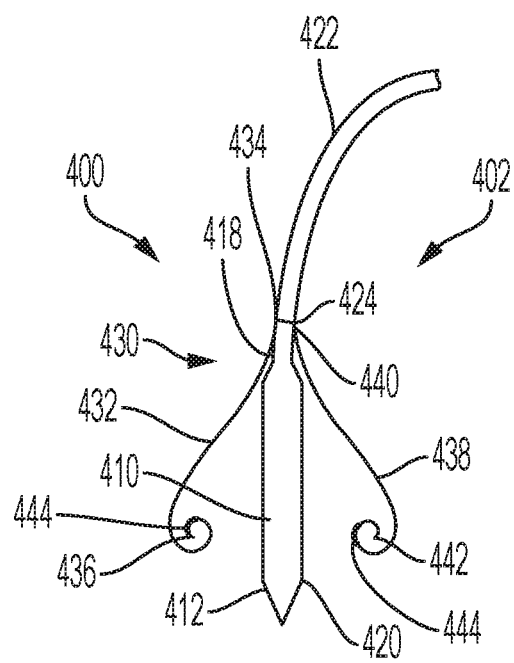
FIG. 9 is a highly schematic side elevational view showing the deployment of an alignment and stabilization device from a delivery device in accordance with yet another embodiment of the present invention.

FIG. 9 illustrates delivery device 400 according to yet another embodiment of the invention. Delivery device 400 has a catheter assembly 402 that is substantially similar to the catheter assembly 202 of delivery device 200. Thus, catheter assembly 402 includes a distal sheath 410 that covers prosthetic heart valve 10 and holds it in a collapsed condition prior to deployment. Distal sheath 410 is affixed at its proximal end to an outer shaft 418, the proximal end of which is connected to an operating handle (not shown). The distal end 420 of distal sheath 410 abuts an atraumatic tip 412 when the distal sheath is in a closed position fully covering prosthetic heart valve 10, and is spaced from the atraumatic tip when the prosthetic heart valve is at least partially uncovered.

An outer tube 422 extends over outer shaft 418 from the handle to a distal or leading end 424 that is close to or abuts the proximal end of distal sheath 410 in a closed condition. Outer tube 422 has a lumen that is sized to define an annular space between outer shaft 418 and the outer tube. The annular space is sized to house an alignment and stabilization device 430 in a collapsed state between outer shaft 418 and outer tube 422.

Delivery device 400 may include all of the other features of delivery device 200 described above but not specifically repeated here. Delivery device 400 differs from delivery device 200 in the structures of their respective alignment and stabilization devices. Alignment and stabilization device 430 includes a first elongated member 432 that extends from a first end 434 coupled to catheter assembly 402 at a spaced distance proximally of distal sheath 410, to a free end 436. The first end 434 of elongated member 432 may be coupled to catheter assembly 402 such that the first end of the elongated member is permitted to slide at least a limited distance in the axial direction relative to outer shaft 418 and, for example, may be coupled to the catheter assembly using any of the mechanisms described above and illustrated in FIGS. 5C-5L. Device 430 may include a second elongated member 438 having a first end 440 coupled to catheter assembly 402 and a free end 442, and may optionally include a third elongated member (not shown) having a first end coupled to the catheter assembly and a free end. The first end 440 of second elongated member 438 and the first end of the third elongated member may be coupled to catheter assembly 402 at substantially the same spaced distance proximally of distal sheath 410 as the first end 434 of first elongated member 432, but at positions that are circumferentially spaced about outer shaft 418. First elongated member 432, second elongated member 438 and the third elongated member preferably have about the same length. The free end 436 of first elongated member 432, the free end 442 of second elongated member 438 and the free end of the third elongated member in an expanded condition may be curled into a pigtail that is sized for insertion into the coronary cusps of the native aortic valve. First elongated member 432, second elongated member 438 and the third elongated member may be formed from a biocompatible material that is capable of self-expansion, for example, a shape memory alloy such as nitinol. Accordingly, alignment and stabilization device 430 may be radially collapsed (e.g., toward outer shaft 418) and inserted into the lumen of outer tube 422 for delivery to the deployment site, and then deployed from the outer tube and radially expanded to engage tissue. A radiopaque marker 444 may be provided on alignment and stabilization device 430, for example on the free end 436 of first elongated member 432, on the free end 442 of second elongated member 438 and/or on the free end of the third elongated member such that the first, second and third elongated members are visible under fluoroscopy and/or echocardiography.

The use of delivery device 400 to align and stabilize prosthetic heart valve 10 within a native valve annulus (e.g., the native aortic annulus) of a patient using a transfemoral approach will now be described with reference to FIGS. 10A and 10B. Although delivery device 400 is described as being delivered to the native aortic valve using a transfemoral approach, it will be understood that the delivery device may be used to deliver a prosthetic heart valve to either of the atrioventricular valves using a transfemoral, transapical, or transseptal approach, or another approach. To load delivery device 400, a physician first collapses and assembles prosthetic heart valve 10 into the catheter assembly 402 of the delivery device such that the leaflets of the prosthetic valve are positioned within the compartment at a predetermined rotational orientation relative to first elongated member 432, second elongated member 438 and the third elongated member that corresponds to the native anatomy of the aortic valve before distal sheath 410 is moved distally to cover the valve. Outer tube 422 may then be slid distally over outer shaft 418 until its distal or leading end 424 abuts or is near to the proximal end of distal sheath 410, collapsing first elongated member 432, second elongated member 438 and the third elongated member within the lumen of the outer tube. Delivery device 400 may then be percutaneously inserted into the patient and advanced toward the native aortic valve using a conventional transfemoral approach.

Figure 10A:
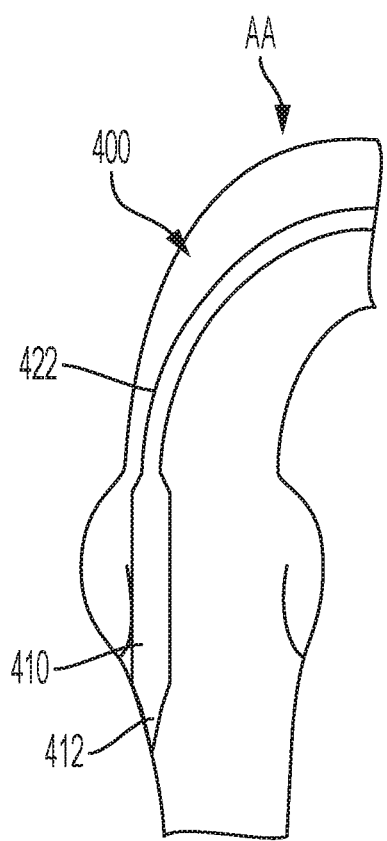
FIGS. 10A and 10B are highly schematic fragmentary views showing the deployment of an alignment and stabilization device in the coronary cusps using the delivery device of FIG. 9 and a transfemoral approach.
Figure 10B:
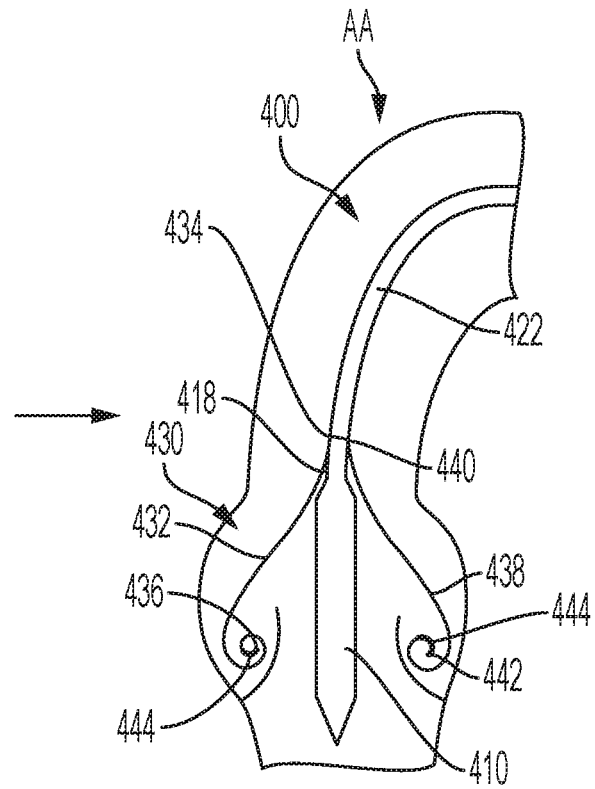

Due to the anatomical curvature of aortic arch AA, distal sheath 410 may approach the native aortic valve AV at an angle to or offset from the center of the native aortic annulus, as shown in FIG. 10A. To ensure proper alignment of distal sheath 410 with the native aortic annulus before the deployment of prosthetic heart valve 10, alignment and stabilization device 430 may first be deployed in the aortic sinus of the patient. Alignment and stabilization device 430 may be deployed by retracting outer tube 422 proximally, exposing the free end 436 of first elongated member 432 and enabling it to curl and radially expand into one of the coronary cusps. The engagement of the curled free end 436 of first elongated member 432 with tissue in the coronary cusp will push or pull distal sheath 410 toward the center of the native valve annulus. The free end 442 of second elongated member 438 and the free end of the third elongated member are simultaneously exposed and radially expand into engagement with the other coronary cusps to prevent distal sheath 410 from moving beyond the center of the native annulus, as shown in FIG. 10B. This engagement will position the distal end 420 of distal sheath 10 and, in turn, prosthetic heart valve 10 at a proper depth within the native valve annulus.

With the first, second and third elongated members disposed within the coronary cusps, the leaflets 38 of prosthetic valve 10 will also be automatically aligned rotationally relative to the leaflets of the patient's native aortic valve. This alignment may be verified by the physician under fluoroscopy and/or echocardiography by visualizing the radiopaque markers 444 on first elongated member 432, second elongated member 438 and the third elongated member. Nevertheless, should the leaflets 38 of prosthetic heart valve 10 need to be adjusted, the physician may rotate delivery device 400 to angularly align the leaflets of the prosthetic heart valve relative to the leaflets of the patient's native aortic valve while using the radiopaque markers 444 on first elongated member 432, second elongated member 438 and/or the third elongated member as a guide. Once the respective leaflets have been aligned, distal sheath 410 may be proximally retracted, exposing the annulus section 18 of stent 12 and enabling it to radially expand into engagement with the native valve annulus. During expansion of the annulus section 18 of stent 12, first elongated member 432, second elongated member 438 and the third elongated member remain engaged with the coronary cusps and absorbs some of the force of the annulus section 18 of the prosthetic heart valve contacting the native valve annulus. With the annulus section 18 of prosthetic heart valve 10 engaged within the native valve annulus, the distal sheath 410 and the alignment and stabilization device 430 may be proximally retracted simultaneously to fully deploy the prosthetic heart valve and remove first elongated member 432, second elongated member 438 and the third elongated member from the coronary cusps. After prosthetic heart valve 10 has been implanted, outer tube 422 may be advanced distally to collapse the first, second and third elongated members within the lumen of outer tube 422, and distal sheath 410 may be advanced distally to a closed position. Delivery device 400 may then be removed from the patient.

Figure 11A:
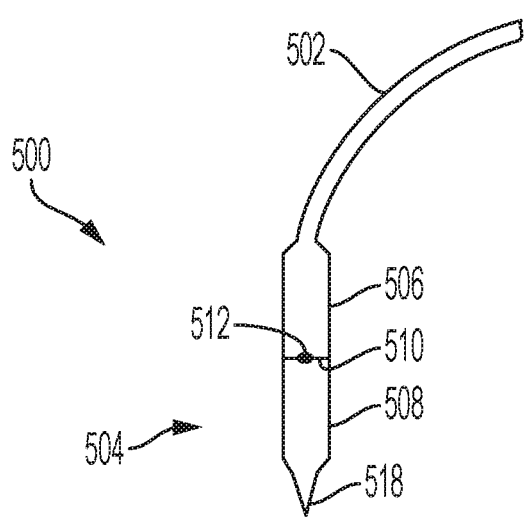
FIGS. 11A and 11B are highly schematic side elevational views showing the deployment of an alignment and stabilization device from a delivery device in accordance with a further embodiment of the present invention.
Figure 11B:
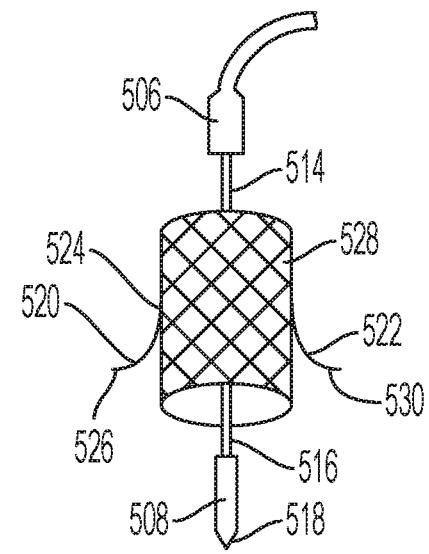

FIGS. 11A and 11B illustrate a delivery device 500 according to a further embodiment of the present invention. Delivery device 500 allows a prosthetic heart valve to be properly aligned and stabilized within a native valve annulus of the patient before the heart valve is fully deployed. As used herein, the term "fully deployed" means the entire heart valve has been withdrawn from the delivery device and transitioned to its expanded state. Delivery device 500 differs from the other delivery devices described above in that it does not itself include an alignment and stabilization device. Rather, alignment and stabilization features are incorporated into prosthetic heart valve 10.

Delivery device 500 includes an outer shaft 502 connected at a proximal end to an operating handle (not shown) and at a distal end to a distal sheath 504. Distal sheath 504 is a split sheath having a proximal sheath section 506 connected to outer shaft 502 and a distal sheath section 508. In a closed condition of distal sheath 504, proximal sheath section 506 abuts distal sheath section 508 at an interface 510, with each sheath section covering a portion of prosthetic heart valve 10 and holding it in a collapsed condition. Distal sheath 504 may include a radiopaque marker 512 at interface 510 so that the joint between proximal sheath section 506 and distal sheath section 508 is visible under fluoroscopy and/or echocardiography. A first inner shaft 514 may be connected at its proximal end to the operating handle, and may extend through a lumen in outer shaft 502 and through the proximal and distal sections of distal sheath 504. Outer shaft 502, proximal sheath section 506 and distal sheath section 508 may be slidable relative to first inner shaft 514. A second inner shaft 516 may also be connected at its proximal end to the operating handle, and may extend slidably through a lumen in first inner shaft 514 and out from the distal end thereof for connection to an atraumatic tip 518. Atraumatic tip 518 is fixedly connected to the distal end of distal sheath section 508 so that sliding movement of second inner shaft 516 relative to first inner shaft 514 in either a proximal or distal direction results in a corresponding movement of the atraumatic tip and the distal sheath section. Delivery device 500 may include all of the other features of the delivery devices described above, such as a compartment for holding prosthetic heart valve 10 and a retainer for receiving the retaining elements 28 of the prosthetic heart valve. However, as noted, delivery device 500 does not include a separate alignment and stabilization device.

Proximal sheath section 506 and distal sheath section 508 are slidable relative to first inner shaft 514 such that they together can selectively cover or uncover the compartment holding prosthetic heart valve 10. Proximal sheath section 506 and distal sheath section 508 fully cover prosthetic heart valve 10 when the proximal sheath section is in its distal-most position and the distal sheath section is in its proximal-most position abutting the proximal sheath section. When proximal sheath section 506 is at least partially retracted proximally or when distal sheath section 508 is at least partially advanced distally, prosthetic heart valve 10 is at least partially exposed for deployment.

As noted above, alignment and stabilization features for this embodiment are incorporated into prosthetic heart valve 10. Referring to FIG. 11B, prosthetic heart valve 10 includes a first elongated member 520 directly coupled to one side of stent 12 and a second elongated member 522 directly coupled to an opposite side of the stent. It will be understood, however, that prosthetic heart valve may include a single elongated member or any number of elongated members greater than one. The following description of a prosthetic heart valve 10 having two elongated members is merely exemplary. The first elongated member 520 is attached at one end 524 to one of the struts 28 of stent 12 in a predetermined one of the annular rows, and has a free end 526 that, in an expanded condition of prosthetic heart valve 10, extends radially outward from the stent for engaging tissue. The end 524 of first elongated member 520 may be attached to one of struts 28 in the annulus section 18 of prosthetic heart valve 10, or alternatively, may be attached to one of the struts at the junction between the annulus section and the transition section 22 of the valve. Similarly, the second elongated member 522 is attached at one end 528 to one of the struts 28 of stent 12, preferably at a location that is diametrically opposed about the stent from the attached end 524 of first elongated member 520, and has a free end 530 that, in an expanded condition of prosthetic heart valve 10, extends radially outward from the stent for engaging tissue.

First elongated member 520 and second elongated member 522 may have substantially the same length, and may be formed from a biocompatible material that is capable of self-expansion, for example, a shape memory alloy such as nitinol. Thus, first elongated member 520 and second elongated member 522 may be collapsed, held in a collapsed condition by proximal sheath section 506 and distal sheath section 508 for delivery to the deployment site, and then deployed from the distal sheath and radially expanded to engage tissue. The free end 526 of first elongated member 520 and the free end 530 of second elongated member 522 may be rounded or curled, for example, to form an atraumatic tip for engaging tissue.

Figure 12A:
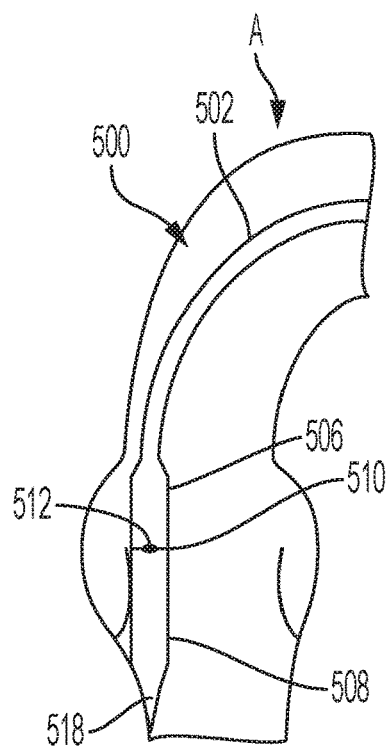
FIGS. 12A-12C are highly schematic fragmentary views showing the deployment of an alignment and stabilization device in the native valve annulus using the delivery device of FIGS. 11A and 11B and a transfemoral approach.
Figure 12B:
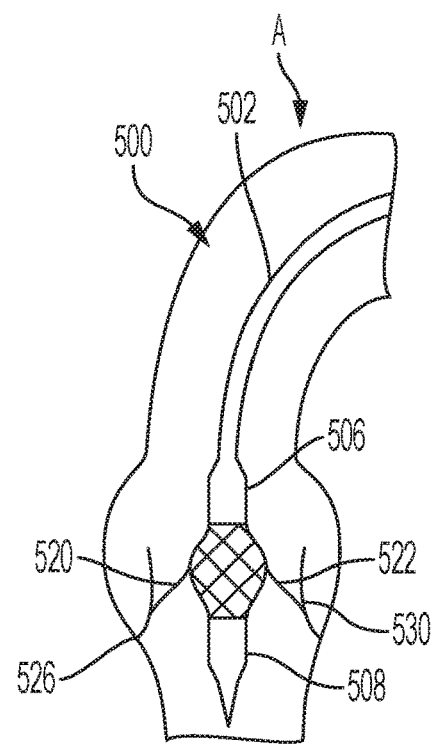
Figure 12C:
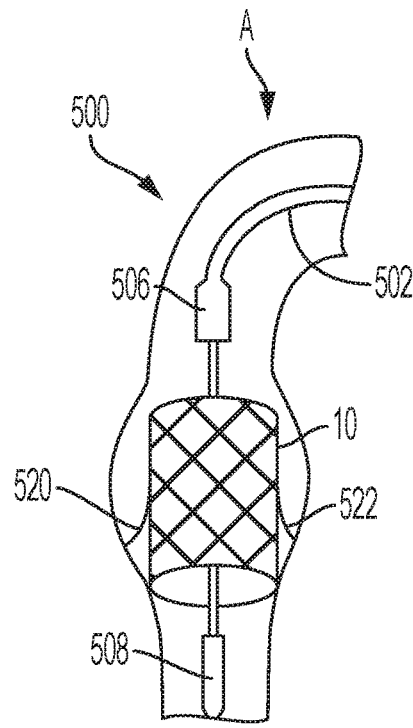

The use of delivery device 500 to align and stabilize a prosthetic heart valve within a native valve annulus of a patient will now be described with reference to FIGS. 12A-12C. Although delivery device 500 is described as being delivered to the native aortic valve using a transfemoral approach, it will be understood that the delivery device may be used to deliver a prosthetic heart valve to either of the atrioventricular valves using a transfemoral, transapical, or transseptal approach, or another approach.

Prosthetic heart valve 10, including elongated members 520 and 522, may be collapsed and assembled around the first inner shaft 514 of delivery device 500 such that the free end 526 of the first elongated member and the free end 530 of the second elongated member face distally toward atraumatic tip 518. While prosthetic heart valve 10 and elongated members 520 and 522 are held in the collapsed condition, proximal sheath section 506 may be slid distally to cover a portion of the valve, and distal sheath section 508 may be slid proximally to cover a remainder of the valve until the proximal and distal sheath sections abut one another at interface 510, as shown in FIG. 12A. Under fluoroscopy and/or echocardiography, a physician may then percutaneously insert delivery device 500 into the patient and guide the delivery device toward the native aortic valve using a transfemoral approach.

Once the physician has determined that radiopaque marker 512 is at the proper location within the native valve annulus, the physician may separate proximal sheath section 506 from distal sheath section 508 to deploy prosthetic heart valve 10. To separate proximal sheath section 506 from distal sheath section 508, the physician may push the second inner shaft 516 of delivery device 500 distally relative to first inner shaft 514, thereby moving distal sheath section 508 distally and away from proximal sheath section 506. As shown in FIG. 12B, second inner shaft 516 may continue to be slid distally by an amount sufficient for distal sheath section 508 to uncover first elongated member 520 and second elongated member 522 and enable their respective free ends 526 and 530 to radially expand and engage the native valve annulus while the aortic section 20 of prosthetic heart valve 10 remains covered by the proximal sheath section 506 of delivery device 500 and while the annulus section 18 of the prosthetic heart valve remains partially covered by the distal sheath section. The engagement of elongated members 520 and 522 with the tissue of the native valve annulus will reposition the distal end of delivery device 500 until it is substantially aligned and centered with the native valve annulus. Subsequently, the physician may further advance second inner shaft 516 and distal sheath section 508 distally and retract outer shaft 502 and proximal sheath section 506 proximally to fully uncover and deploy prosthetic heart valve 10. Because first elongated member 520 and second elongated member 522 are stabilized against the native aortic annulus as the annulus section 18 of prosthetic heart valve 10 contacts the annulus, the prosthetic heart valve is less susceptible to becoming repositioned upon contacting the annulus. After prosthetic heart valve 10 has been implanted, second inner shaft 516 and distal sheath section 508 may be retracted and outer shaft 502 and proximal sheath section 506 may be advanced until the sheath sections abut one another at interface 510. Thereafter, delivery device 500 may be removed from the patient.

To summarize the foregoing, a delivery device for a collapsible prosthetic heart valve includes a catheter assembly, the catheter assembly including an inner shaft around which a compartment is defined, the compartment being adapted to receive the prosthetic heart valve in an assembled condition; an outer shaft assembled over the inner shaft and adapted to slide relative to the inner shaft along a longitudinal axis thereof; a distal sheath connected to a distal end of the outer shaft and slidable therewith, the distal sheath being adapted to selectively cover and uncover the compartment and the prosthetic heart valve when the prosthetic heart valve is in the assembled condition; and an outer tube assembled over the outer shaft; and an alignment and stabilization device having a collapsed condition and an expanded condition, the alignment and stabilization device having one end coupled to the catheter assembly proximally of the compartment, wherein the outer tube is adapted to slide relative to the outer shaft to selectively cover and uncover the alignment and stabilization device; and/or the alignment and stabilization device may be formed of braided nitinol; and/or the alignment and stabilization device may be substantially funnel shaped in the expanded condition, and the alignment and stabilization device may have a longitudinal axis that is coaxial with the outer shaft in the expanded condition; and/or the alignment and stabilization device may be covered by one or more layers of a porous material; and/or the alignment and stabilization device may include a radiopaque marker; and/or the alignment and stabilization device may include a first elongated member having a first end coupled to the catheter assembly and a free end, the free end in the expanded condition being spaced apart from the outer shaft; and/or the alignment and stabilization device may further include a second elongated member having a first end coupled to the catheter assembly and a free end, the first end of the second elongated member being coupled to the catheter assembly at a location circumferentially spaced from the first end of the first elongated member, the free end of the second elongated member in the expanded condition being spaced apart from the outer shaft; and/or the free ends of the first and second elongated members in the expanded condition may have a curled configuration; and/or the device may further include a collapsible and expandable prosthetic heart valve assembled in the compartment; and/or the alignment and stabilization device may be spaced from the prosthetic heart valve when the prosthetic heart valve is assembled in the compartment and the alignment and stabilization device is in the expanded condition.

In another embodiment, a delivery device for a collapsible prosthetic heart valve includes a valve sheath having a lumen configured to receive a collapsible and expandable prosthetic heart valve; an inner member having a length extending along a longitudinal axis, the inner member being at least partially disposed within the lumen; and a stabilization device having a collapsed condition and an expanded condition, the stabilization device being attached to the inner member at a predetermined location along the length of the inner member; and/or the stabilization device may be formed of braided nitinol; and/or the stabilization device may be substantially funnel shaped, and the stabilization device may have a longitudinal axis that is coaxial with the valve sheath in the expanded condition; and/or the valve sheath may include a capsule and the stabilization device may be configured to be received within the capsule in the collapsed condition; and/or the stabilization device may be covered by a porous membrane.

In yet another embodiment, a delivery device for stabilizing a heart valve includes a delivery tube extending in a longitudinal direction and including a leading portion and a trailing portion, the leading portion and the trailing portion being separable from one another and together defining a lumen configured to receive a heart valve; a deployment device at least partially received within the lumen of the delivery tube, the deployment device including a first member and a second member slidable relative to the first member; a valve including a stent and a valve assembly, the stent including a plurality of struts forming cells; and a stabilization device, the stabilization device including a first elongated collapsible and expandable member having an attached end connected to the stent and a free end for engaging tissue; and/or the stabilization device may further include a second elongated collapsible and expandable member having an attached end connected to the stent at a location that diametrically opposes the attached end of the first collapsible and expandable member, and a free end for engaging tissue; and/or the leading portion of the delivery tube and the trailing portion of the delivery tube may be removably coupled to one another along an interface, the interface including a radiopaque marker; and/or the first member of the deployment device may be connected to the leading portion of the delivery tube and the second member of the deployment device may be connected to the trailing portion of the delivery tube such that relative movement of the first member away from the second member separates the leading portion of the delivery tube from the trailing portion of the delivery tube.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A delivery device for a collapsible prosthetic heart valve, comprising:
  a catheter assembly comprising:
    an inner shaft around which a compartment is defined, the compartment being adapted to receive the prosthetic heart valve in an assembled condition;
    an outer shaft assembled over the inner shaft and adapted to slide relative to the inner shaft along a longitudinal axis thereof;
    a distal sheath connected to a distal end of the outer shaft and slidable therewith, the distal sheath being adapted to selectively cover and uncover the compartment and the prosthetic heart valve when the prosthetic heart valve is in the assembled condition; and
    an outer tube assembled over the outer shaft; and
  an alignment and stabilization device having a collapsed condition and an expanded condition, the alignment and stabilization device having one end connected to the outer shaft proximally of the compartment so that the alignment and stabilization device is slidable in a longitudinal direction relative to the outer shaft,
  wherein the outer tube is adapted to slide relative to the outer shaft to selectively cover and uncover the alignment and stabilization device.

2. The device of claim 1, wherein the alignment and stabilization device is formed of braided nitinol.

3. The device of claim 1, wherein the alignment and stabilization device is substantially funnel shaped in the expanded condition, and the alignment and stabilization device has a longitudinal axis that is coaxial with the outer shaft in the expanded condition.

4. The device of claim 3, wherein the alignment and stabilization device includes one or more layers of a porous material.

5. The device of claim 1, wherein the alignment and stabilization device includes a radiopaque marker.

6. The device of claim 1, wherein the alignment and stabilization device includes a first elongated member having a free end, the free end in the expanded condition being spaced apart from the outer shaft.

7. The device of claim 6, wherein the alignment and stabilization device further includes a second elongated member having a free end, the second elongated member being connected to the outer shaft at a location that is circumferentially spaced from the first elongated member, the free end of the second elongated member in the expanded condition being spaced apart from the outer shaft.

8. The device of claim 7, wherein the free ends of the first and second elongated members in the expanded condition have a curled configuration.

9. A prosthetic heart valve delivery system, comprising:
the delivery device of claim 1; and
a collapsible and expandable prosthetic heart valve assembled in the compartment.

10. The system of claim 9, wherein the alignment and stabilization device is spaced from the prosthetic heart valve when the prosthetic heart valve is assembled in the compartment and the alignment and stabilization device is in the expanded condition.

* * * * *